(12) United States Patent
Zhang et al.

(10) Patent No.: US 12,338,651 B2
(45) Date of Patent: Jun. 24, 2025

(54) DISINFECTION DEVICE OF DOOR HANDLE BEING ROTATIONAL AND TRANSPOSITIONAL

(71) Applicant: DALIAN UNIVERSITY OF TECHNOLOGY, Dalian (CN)

(72) Inventors: Tengfei Zhang, Dalian (CN); Di Xiao, Dalian (CN); Jihong Wang, Dalian (CN); Shugang Wang, Dalian (CN)

(73) Assignee: DALIAN UNIVERSITY OF TECHNOLOGY, Dalian (CN)

( * ) Notice: Subject to any disclaimer, the term of this patent is extended or adjusted under 35 U.S.C. 154(b) by 493 days.

(21) Appl. No.: 17/982,079

(22) Filed: Nov. 7, 2022

(65) Prior Publication Data

US 2023/0058131 A1    Feb. 23, 2023

(30) Foreign Application Priority Data

Mar. 17, 2022 (CN) .......................... 202210264685.5

(51) Int. Cl.
*E05B 1/00* (2006.01)
*A61L 2/10* (2006.01)

(52) U.S. Cl.
CPC .............. *E05B 1/0069* (2013.01); *A61L 2/10* (2013.01); *A61L 2202/11* (2013.01); *A61L 2202/14* (2013.01)

(58) Field of Classification Search
CPC ................................. E05B 1/0069; A61L 2/10
See application file for complete search history.

(56) References Cited

FOREIGN PATENT DOCUMENTS

| CN | 103015791 A | 4/2013 |
|---|---|---|
| CN | 111852182 A | 10/2020 |
| CN | 213205282 U | 5/2021 |

OTHER PUBLICATIONS

English Translation of Foreign Patent Document No. CN 213205282 U provided by the USPTO search software PE2E Search; Li, Junyuan et al.; Handle Device of Automatic Sterilizing Door; May 14, 2021 (Year: 2021).*

* cited by examiner

*Primary Examiner* — Kevin Joyner
(74) *Attorney, Agent, or Firm* — MUNCY, GEISSLER, OLDS & LOWE, P.C.

(57) ABSTRACT

The present invention relates to a disinfection device of door handle being rotational and transpositional, the composition is as follows: a plurality of door handles are provided, which are respectively in the states of "to be used", "in disinfection", "in disinfection post-treatment" and/or "in ready"; and the door handle transposition shaft is driven by the rotary driving device of door handle transposition shaft to rotate counterclockwise, thus to complete synchronous rotation of the door handles and realize transposition operation. The use, disinfection and disinfection post-treatment of the door handles of the present invention are carried out synchronously, which can meet the requirements of immediate use of the door handles and safety to the users; the transposition of the door handles is implemented by the pure mechanical driving device; the door handles automatically rotates for transposition after a door opening and closing, therefore "disinfection after each use" is realized.

5 Claims, 5 Drawing Sheets

DISINFECTION DEVICE OF DOOR HANDLE BEING ROTATIONAL AND TRANSPOSITIONAL

TECHNICAL FIELD

The present invention relates to the technical field of disinfection and epidemic prevention, and particularly relates to a disinfection device of door handle being rotational and transpositional after door opening and closing.

BACKGROUND

As a tool for opening a door, a door handle is easy to breed and accumulate germs after frequent contact, especially in public places with a huge visitors flow rate, such as schools, hospitals and shopping malls. The germs attached to the door handle has the characteristics of rapid breeding, numerous varieties and large number, and the door handle has become an important vector of disease transmission. During the COVID-19 epidemic, the risk of cross-infection of germs through door handles has been greatly increased, so door handle disinfection is a necessary measure to cut off the transmission route of germs.

At present, the most popular method for door handle disinfection is spraying disinfectant manually; such a disinfection method not only consumes manpower and material resources, but also has a short effective duration, which makes it impossible to realize "disinfection after each use". In some public places, the method of placing wash-free hand sanitizer by the door is adopted; such a disinfection method depends on the subjectivity of people passing in and out, and the disinfection effect is even less optimistic.

In view of the above problems, some inventors have proposed self-disinfecting door handles. Patent CN111852182A proposes a door handle capable of being automatically disinfected by heating according to multiple preset time intervals, which requires no manual participation or consumables during disinfection, so the disinfection effect is improved, and the disinfection cost is reduced. However, this door handle cannot be used during disinfection, which is inconvenient; in addition, "disinfection after each use" cannot be realized for this door handle, therefore a hidden danger of cross-infection of germs still exists. Patent CN213205282U proposes door handles capable of being replaced with each other in alternating cycles, wherein two door handles are respectively in the states of "in disinfection" and "in ready", but the door handles need to be driven by a stepper motor, and the structure is relatively complex. Patent CN103015791A proposes a door handle with an ultraviolet lamp turned on at leisure and turned off in use; "disinfection after each use" is realized for this door handle, but the cost of ultraviolet disinfection is high, and the door handle cannot be completely disinfected when a door is frequently opened and closed.

The present invention aims to solve the above problems, and develops a disinfection device of door handle being rotational and transpositional.

SUMMARY

Aiming at the defects of the prior art, the present invention provides a door handle capable of automatic rotation and transposition for disinfection after door opening and closing, which does not affect the use, and can realize "disinfection after each use".

The present invention is realized by the following technical solution:

A disinfection device of door handle being rotational and transpositional, comprising door handles 1, a door handle transposition shaft 2, a switch lock shaft 3, an unlocking device 4, a rotary driving device of door handle transposition shaft 5, a disinfection device 6 and a disinfection post-treatment device 7; a plurality of door handles 1 are provided and connected with the door handle transposition shaft 2, and the door handles 1 are respectively in the states of "to be used", "in disinfection", "in disinfection post-treatment" and/or "in ready"; the unlocking device 4 is connected with the switch lock shaft 3, and the switch lock shaft 3 is connected with the door handle transposition shaft 2; and the door handle transposition shaft 2 is driven by the rotary driving device of door handle transposition shaft 5 to rotate counterclockwise, thus to complete synchronous rotation of the door handles 1 and realize transposition operation.

The inner end of the door handles 1 is fixed with a shaft sleeve by a short shaft, the door handles 1 are evenly distributed along the door handle transposition shaft 2, the inner end of which is fixed with a shaft sleeve by a short shaft, coaxially connected to the door handle transposition shaft 2 by the shaft sleeve, nested in the arc groove of the door handle transposition shaft 2 by the short shaft, and can rotate around the axis of the door handle transposition shaft 2 along the arc groove.

The door handle transposition shaft 2 comprises a turntable and a driven sheave of a geneva mechanism which are coaxially connected, the turntable is provided with an arc groove, the switch lock shaft 3 is coaxially connected with the door handle transposition shaft 2 through a ratchet mechanism, a ratchet of which is fixedly sleeved on the switch lock shaft 3, and a pawl of which is fixed on the driven sheave of the door handle transposition shaft 2; when a door is opened, the door handle transposition shaft 2 rotates clockwise, and the switch lock shaft 3 rotates synchronously; whenthe door is closed, the door handle transposition shaft 2 is driven by the switch lock shaft 3 to rotate counterclockwise; when the door handles 1 rotates for transposition, the door handle transposition shaft 2 rotate counterclockwise, and the switch lock shaft 3 is stationary.

A dial 3-1 is fixed at the position between the end of the switch lock shaft 3 and the ratchet of the ratchet mechanism.

The unlocking device 4 can only do linear reciprocating motion, and is used for controlling the opening and closing of the door; the unlocking device 4 comprises a switch bolt 4-1, a connecting rod of bolt 4-2 and a spring 4-3; the switch bolt 4-1 is fixedly connected with one end of the connecting rod of bolt 4-2, and the spring 4-3 is sleeved on one end of the connecting rod of bolt 4-2 that is closed to the switch bolt 4-1, and is used for controlling the reset of the switch bolt 4-1; the other end of the connecting rod of bolt 4-2 is provided with a stopper, and the dial 3-1 pushes the stopper when rotating, thus driving the unlocking device 4 to move.

The rotary driving device of door handle transposition shaft 5 comprises a door handle transposition driving bolt 5-1, a displacement extension transmission device and a driving device that turns straight into rotation; the displacement extension transmission device comprises a driving rack 5-2, a driving gear 5-3, a driven gear 5-4, a driven rack 5-5 and a spring 5-6; the driving device that turns straight into rotation comprises the driven rack 5-5, a connecting rod 5-7 and a crank 5-8; the door handle transposition driving bolt 5-1 is fixedly connected with one end of the driving rack 5-2, the driving rack 5-2 is meshed with the driving gear 5-3, the driving gear 5-3 and the driven gear 5-4 are coaxially and fixedly connected, and the transmission ratio of the two is less than 1; the driven gear 5-4 is meshed with the driven rack 5-5, and the spring 5-6 is arranged at the other end of the driving rack 5-2 and is used for controlling the reset of the door handle transposition driving bolt 5-1; the driven rack 5-5, the connecting rod 5-7 and the crank 5-8 form a crank-slider mechanism, the driven rack 5-5 is rotationally connected with one end of the connecting rod 5-7, the other end of the connecting rod 5-7 is rotationally connected with the crank 5-8, and the other end of the crank 5-8 is fixed; the linear motion of the driven rack 5-5 pushes the connecting rod 5-7 to drive the crank 5-8 to rotate around the fixed end, a round pin of the geneva mechanism is fixed at the joint of the connecting rod 5-7 and the crank 5-8, and the round pin is intermittently inserted into a notch of the driven sheave along with the rotation of the crank 5-8 to control the intermittent counterclockwise rotation of the door handle transposition shaft 2; the short-distance linear reciprocating motion of the door handle transposition driving bolt 5-1 is converted into the long-distance linear reciprocating motion of the driven rack 5-5 by the displacement extension transmission device, and then converted into the clockwise rotation motion of the crank 5-8 by the driving device that turns straight into rotation, which is used to control the intermittent counterclockwise rotation of the door handle transposition shaft 2.

The disinfection method of the disinfection device 6 includes but is not limited to heating disinfection, ultraviolet disinfection or disinfectant disinfection.

When heating disinfection is adopted, a temperature controller and a time relay are provided in the disinfection device 6, the heating temperature is controlled by the temperature controller, and the heating time is controlled by the time relay, the back end of the disinfection device 6 is provided with the disinfection post-treatment device 7, and the disinfection post-treatment device 7 is a cooling fan;

When ultraviolet disinfection is adopted, a ultraviolet lamp and a time relay are provided in the disinfection device 6, the ultraviolet irradiation time is controlled by the time relay, and the disinfection post-treatment device 7 is not needed;

When disinfectant disinfection is adopted, a disinfectant storage tank, a spray device and an inductive switch are provided in the disinfection device 6, the spray of disinfectant is controlled by the inductive switch, the back end of the disinfection device 6 is provided with the disinfection post-treatment device 7, and the disinfection post-treatment device 7 is a fan for drying.

The present invention has the following beneficial effects:
1. The use, disinfection and disinfection post-treatment of the door handles are carried out synchronously, which can meet the requirements of immediate use and safety of the door handles.
2. No extra electric drive is needed, and the transposition operation of the door handles is completed by the pure mechanical rotary driving device, so the structure is simple.
3. The door handles will rotate automatically for transposition after a door opening and closing, therefore "disinfection after each use" is realized.

Figure 1:
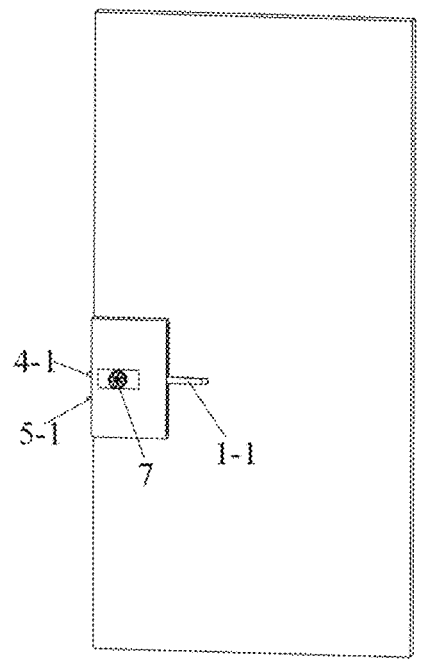
FIG. 1 is a schematic diagram of a door after the present invention is installed.
Figure 2:
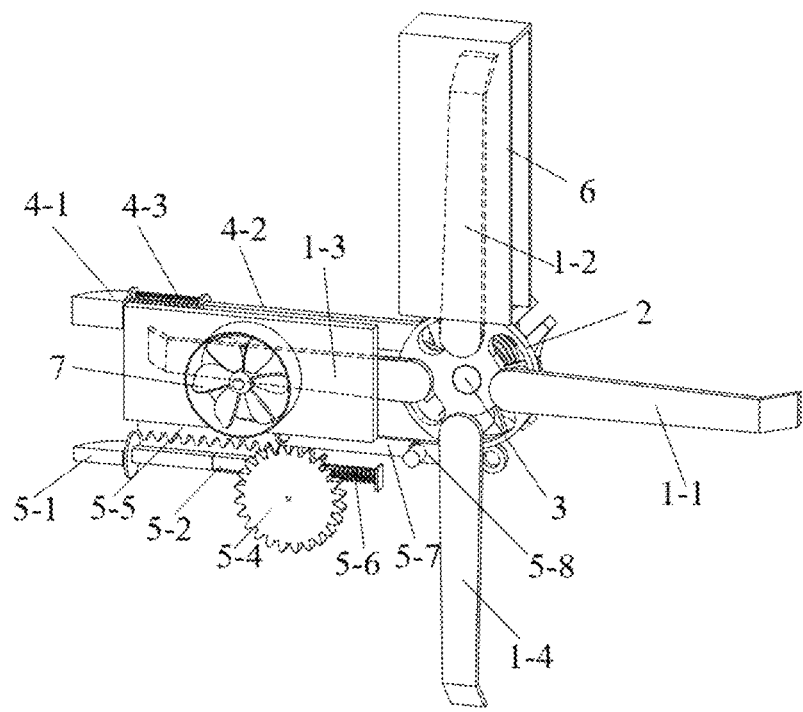
FIG. 2 is an integral schematic diagram of the present invention.
Figure 3:
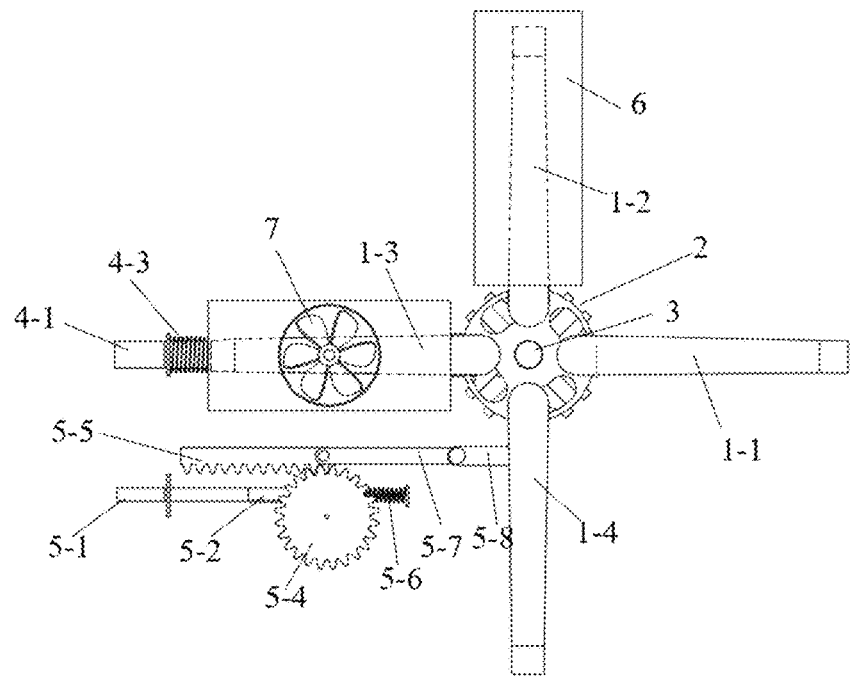
FIG. 3 is a front view of the present invention.
Figure 4:
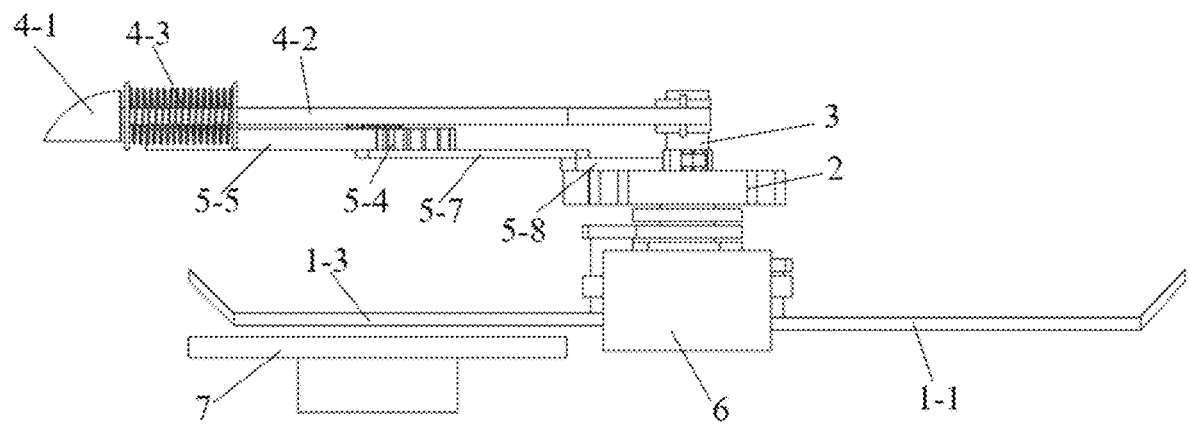
FIG. 4 is a top view of the present invention.
Figure 5:
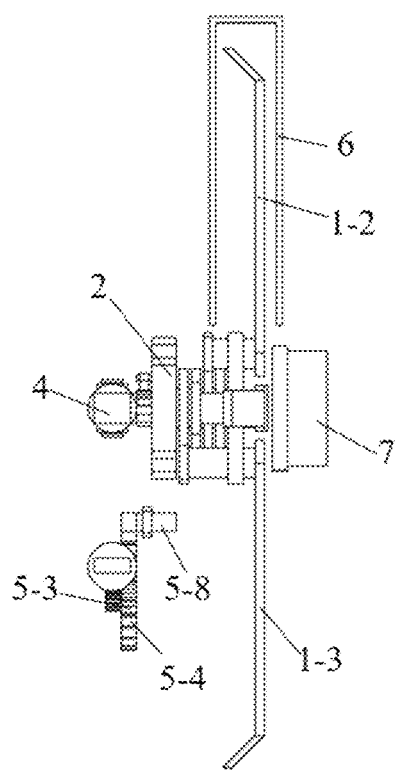
FIG. 5 is a left view of the present invention.
Figure 6:
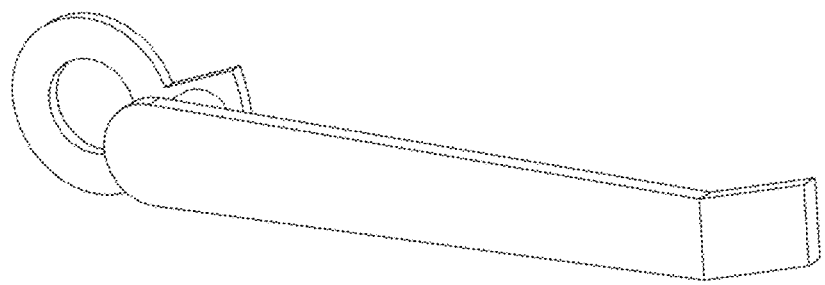
FIG. 6 is a schematic diagram of a door handle of the present invention.
Figure 7:
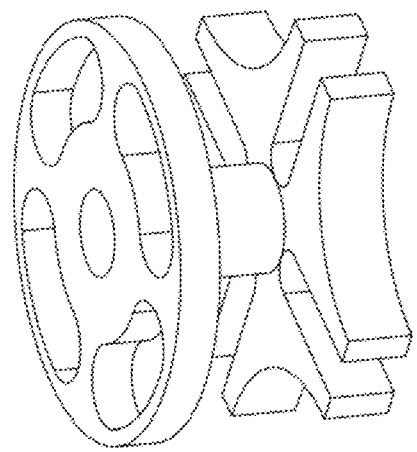
FIG. 7 is a schematic diagram of a door handle transposition shaft used for controlling door handles of the present invention.

In the figures: 1. door handle; 1-1. door handle to be used; 1-2. door handle in disinfection; 1-3. door handle in disinfection post-treatment; 1-4. door handle in ready; 2. door handle transposition shaft; 3. switch lock shaft; 3-1. dial; 4. unlocking device; 4-1. switch bolt; 4-2. connecting rod of bolt; 4-3. spring; 5. rotary driving device of door handle transposition shaft; 5-1. door handle transposition driving bolt; 5-2. driving rack; 5-3. driving gear; 5-4. driven gear; 5-5. driven rack; 5-6. spring; 5-7. connecting rod; 5-8. crank; 6. disinfection device; 7. disinfection post-treatment device.

DETAILED DESCRIPTION

To make the purpose, the technical solution and the advantages of the present application more clear, the present invention is further described below in detail with reference to the drawings and the listed embodiments.

As shown in FIGS. 1-5, a disinfection device of door handle being rotational and transpositional, consisting of door handles 1, a door handle transposition shaft 2, a switch lock shaft 3, an unlocking device 4, a rotary driving device of door handle transposition shaft 5, a disinfection device 6 and a disinfection post-treatment device 7. Four door handles are provided, including a door handle to be used 1-1, a door handle in disinfection 1-2, a door handle in disinfection post-treatment 1-3 and a door handle in ready 1-4, which are coaxially connected, respectively nested in an arc groove of the door handle transposition shaft 2, evenly distributed along the door handle transposition shaft 2, and can rotate around the axis of the door handle transposition shaft 2 along the arc groove. Only one door handle rotates during door opening and closing, and all of the door handles rotate simultaneously during transposition operation. The door handle transposition shaft 2 and the rotary driving device 5 thereof are connected by a geneva mechanism.

Figure 8:
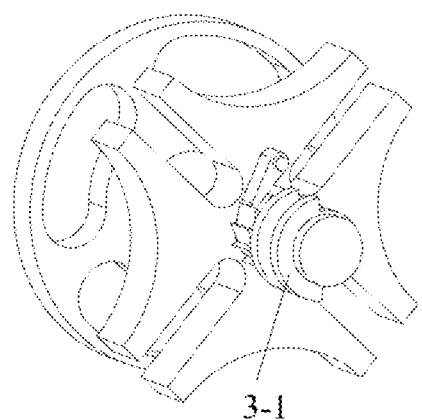
FIG. 8 is a schematic diagram of connecting a door handle transposition shaft with a switch lock shaft of the present invention.

As shown in FIG. 8, the door handle transposition shaft 2 is coaxial with the switch lock shaft 3, and the two are connected by a ratchet mechanism; when the door is closed, the door handle transposition shaft 2 rotates clockwise, and the switch lock shaft 3 rotates synchronously; when the door is closed, the door handle transposition shaft 2 is driven by the switch lock shaft (3) to rotate counterclockwise; when the door handles 1 rotates for transposition, the door handle transposition shaft 2 rotate counterclockwise, and the switch lock shaft 3 is stationary.

Figure 9:
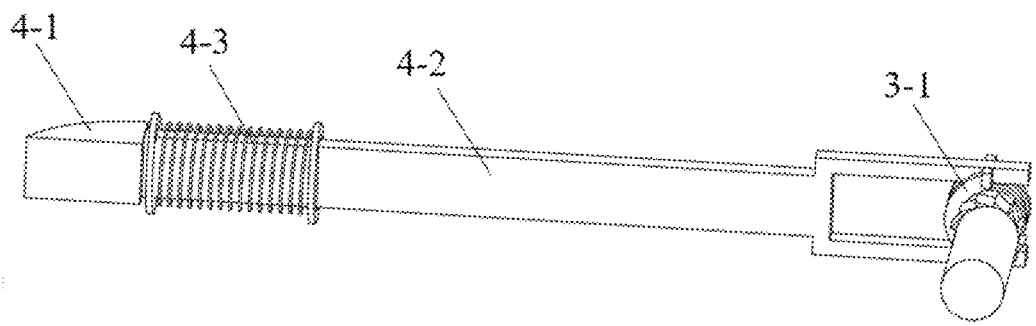
FIG. 9 is a schematic diagram of connecting a switch lock shaft with an unlocking device of the present invention.

As shown in FIG. 9, the motion of the unlocking device 4 is controlled by the switch lock shaft 3 through a dial 3-1, and the unlocking device 4 is used for controlling the opening and closing of the door. The unlocking device 4 comprises a switch bolt 4-1, a connecting rod of bolt 4-2 and a spring 4-3; the switch bolt 4-1 is fixedly connected with the connecting rod of bolt 4-2 and can only do linear reciprocating motion, and the spring 4-3 is used for controlling the reset of the switch bolt.

Figure 10:
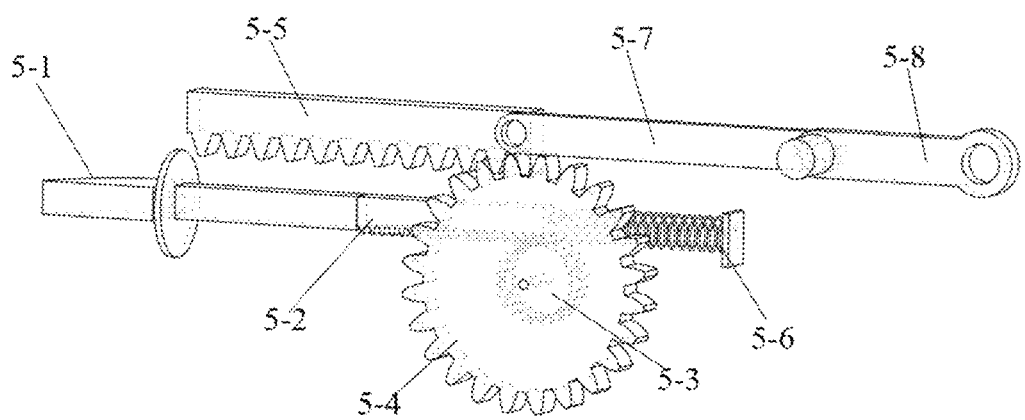
FIG. 10 is a schematic diagram of a rotary driving device of door handle transposition shaft of the present invention.

As shown in FIG. 10, the rotary driving device of door handle transposition shaft 5 comprises a door handle transposition driving bolt 5-1, a driving rack 5-2, a driving gear 5-3, a driven gear 5-4, a driven rack 5-5, a connecting rod 5-7, a crank 5-8 and a spring 5-6; the door handle transposition driving bolt 5-1 is fixedly connected with the driving rack 5-2, the driving rack 5-2 is meshed with the driving gear 5-3, the driving gear 5-3 and the driven gear 5-4 are coaxially and fixedly connected, and the transmission ratio of the two is 1:3; the driven gear 5-4 is meshed with the driven rack 5-5 to convert the short-distance linear motion of the door handle transposition driving bolt 5-1 into the long-distance linear motion of the driven rack 5-5, and the spring 5-6 is used for controlling the reset of the door handle transposition driving bolt; the driven rack 5-5, the connecting rod 5-7 and the crank 5-8 form a crank-slider mechanism to convert the linear motion of the driven rack 5-5 into the clockwise rotation motion of the crank 5-8, which is used to control the intermittent counterclockwise rotation of the door handle transposition shaft 2.

Figure 11:
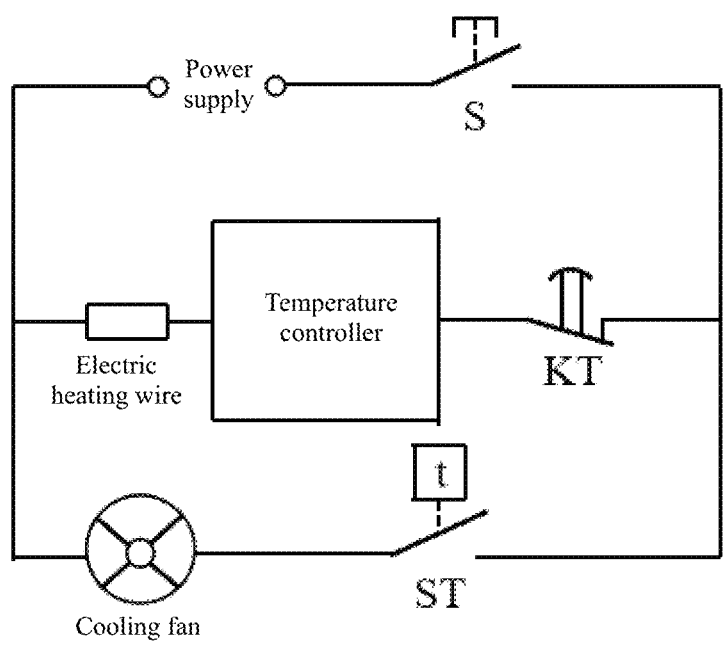
FIG. 11 is a circuit diagram of a disinfection device and a disinfection post-treatment device of the present invention.

The disinfection method of the disinfection device 6 in the embodiment is infrared heating disinfection, the disinfection device 6 is internally provided with a temperature controller and a time relay, and the disinfection post-treatment device 7 is a cooling fan, which is internally provided with a temperature control switch. As shown in FIG. 11, the infrared heating disinfection device 6 is connected in parallel with the cooling fan 7. A contact switch S and the temperature control switch ST in a circuit of the cooling fan 7 is normally off, and a contact of the time relay KT in a circuit of the infrared heating disinfection device 6 is a normally-on delay-off contact. The contact switch S is arranged on a round pin of the crank 5-8; when the round pin is at the rightmost position, i.e., when the door is closed, the contact switch S is switched on, and the infrared heating disinfection device 6 is energized; the temperature of an electric heating wire is controlled by the temperature controller to be not less than 56° C., and the time relay KT is timed for 30 min; after 30 min, the time relay KT is disconnected, and disinfection stops. The temperature control switch ST in the circuit of the cooling fan 7 is switched on when the temperature sensed reaches 45° C., and the cooling fan is started; when the temperature sensed is lower than 45° C., the cooling fan is stopped.

The present invention works as follows: when the door is opened, the door handle transposition shaft 2 is driven by the door handle to be used 1-1 to rotate clockwise, thus driving the switch lock shaft 3 and the unlocking device 4 in turns to complete a door opening action. Specifically, when the door is opened, the door handle to be used 1-1 rotates clockwise and applies a pressure to the arc groove of the door handle transposition shaft 2 through a short shaft, thus driving the door handle transposition shaft 2 to rotate synchronously clockwise; a pawl on the door handle transposition shaft 2 pushes a ratchet on the switch lock shaft 3, thus driving the switch lock shaft 3 to rotate clockwise; the dial 3-1 on the switch lock shaft 3 is driven by the switch lock shaft 3 to rotate clockwise, and a stopper arranged on one end of the connecting rod of bolt 4-2 is pushed by the dial 3-1, thus driving the unlocking device 4 to move; at this time, the switch bolt 4-1 of the unlocking device 4 is drawn out from a lock slot in a door frame.

After the door opening action is completed, the switch bolt 4-1 is reset under the action of the spring 4-3, and the connecting rod of bolt 4-2, the switch lock shaft 3, the door handle transposition shaft 2 and the door handle to be used 1-1 are driven to reset in turns, thus to complete a door closing action. Specifically, when the door is closed, the switch bolt 4-1 is reset under the action of the spring 4-3, thus driving the connecting rod of bolt 4-2 to move; the dial 3-1 on the switch lock shaft 3 is pushed by the stopper on the connecting rod of bolt 4-2 to drive the switch lock shaft 3 to rotate counterclockwise, the pawl on the door handle transposition shaft 2 is pushed by the ratchet on the switch lock shaft 3 to drive the door handle transposition shaft 2 to rotate counterclockwise, and the door handle 1-1 is driven by the door handle transposition shaft 2 to rotate counterclockwise and reset. During door opening and closing, the door handle in disinfection 1-2, the door handle in disinfection post-treatment 1-3 and the door handle in ready 1-4 are stationary.

After the door is closed, the door handle transposition driving bolt 5-1 is squeezed by the door frame to move straight to the right, thus driving the driving rack 5-2, the driving gear 5-3, the driven gear 5-4 and the driven rack 5-5 to move. Specifically, the driving rack 5-2 is driven by the door handle transposition driving bolt 5-1 to move straight to the right, the driving gear 5-3 is driven by the driving rack 5-2 to rotate clockwise, the driven gear 5-4 is driven by the driving gear 5-3 to rotate clockwise, the driven rack 5-5 is driven by the driven gear 5-4 to move straight to the right, the short-distance linear motion of the door handle transposition driving bolt 5-1 is converted into the long-distance linear motion of the driven rack 5-5, the driven rack 5-5 is used as a slider of the crank-slider mechanism to drive the crank 5-8 to rotate clockwise through the connecting rod 5-7, the round pin of the crank 5-8 rotates clockwise and is inserted into a notch of a driven sheave of the door handle transposition shaft 2 to drive the door handle transposition shaft 2 to rotate counterclockwise, and the four door handles 1 are driven by the door handle transposition shaft 2 to rotate 90 degrees counterclockwise, thus the transposition operation of the door handles is completed. At this time, the door handle transposition driving bolt 5-1 is at the rightmost position of a stroke, i.e., the round pin of the crank 5-8 is at the rightmost position, the contact switch S is switched on, the infrared heating disinfection device 6 is started, disinfection is timed for 30 min, and the cooling fan 7 is started when the temperature sensed by the temperature control switch of the cooling fan 7 reaches 45° C. After the door is opened and closed, a door handle used will be used again by a user after automatic rotation and transposition, heating disinfection and cooling.

The invention claimed is:

1. A disinfection device of door handle being rotational and transpositional, comprising door handles (1), a door handle transposition shaft (2), a switch lock shaft (3), an unlocking device (4), a rotary driving device of door handle transposition shaft (5), a disinfection device (6) and a disinfection post-treatment device (7); the door handles (1) are provided and connected with the door handle transposition shaft (2), and the door handles (1) are respectively in the states of to be used, in disinfection, in disinfection post-treatment and/or in ready; the unlocking device (4) is connected with the switch lock shaft (3), and the switch lock shaft (3) is connected with the door handle transposition shaft (2); the door handle transposition shaft (2) is driven by the rotary driving device of door handle transposition shaft (5) to rotate counterclockwise, thus to complete synchronous rotation of the door handles (1) and realize transposition operation;

the door handle transposition shaft (2) comprises a turntable and a driven sheave of a geneva mechanism which are coaxially connected, the turntable is provided with an arc groove, the switch lock shaft (3) is coaxially connected with the door handle transposition shaft (2) through a ratchet mechanism, a ratchet of which is fixedly sleeved on the switch lock shaft (3), and a pawl of which is fixed on the driven sheave of the door handle transposition shaft (2); when a door is opened, the door handle transposition shaft (2) rotates clockwise, and the switch lock shaft (3) rotates synchronously; when the door is closed, the door handle transposition shaft (2) is driven by the switch lock shaft (3) to rotate counterclockwise; when the door handles (1) rotates for transposition, the door handle transposition shaft (2) rotate counterclockwise, and the switch lock shaft (3) is stationary;

a dial (3-1) is fixed at the position between the end of the switch lock shaft (3) and the ratchet of the ratchet mechanism;

the rotary driving device of door handle transposition shaft (5) comprises a door handle transposition driving bolt (5-1), a displacement extension transmission device and a driving device that turns straight into rotation; the displacement extension transmission device comprises a driving rack (5-2), a driving gear (5-3), a driven gear (5-4), a driven rack (5-5) and a spring (5-6); the driving device that turns straight into rotation comprises the driven rack (5-5), a connecting rod (5-7) and a crank (5-8); the door handle transposition driving bolt (5-1) is fixedly connected with one end of the driving rack (5-2), the driving rack (5-2) is meshed with the driving gear (5-3), the driving gear (5-3) and the driven gear (5-4) are coaxially and fixedly connected, and the transmission ratio of the two is less than 1; the driven gear (5-4) is meshed with the driven rack (5-5), and the spring (5-6) is arranged at the other end of the driving rack (5-2) and is used for controlling the reset of the door handle transposition driving bolt (5-1); the driven rack (5-5), the connecting rod (5-7) and the crank (5-8) form a crank-slider mechanism, the driven rack (5-5) is rotationally connected with one end of the connecting rod (5-7), the other end of the connecting rod (5-7) is rotationally connected with the crank (5-8), and the other end of the crank (5-8) is fixed; the linear motion of the driven rack (5-5) pushes the connecting rod (5-7) to drive the crank (5-8) to rotate around the fixed end, a round pin of the geneva mechanism is fixed at the joint of the connecting rod (5-7) and the crank (5-8), and the round pin is intermittently inserted into a notch of the driven sheave along with the rotation of the crank (5-8) to control the intermittent counterclockwise rotation of the door handle transposition shaft (2); the short-distance linear reciprocating motion of the door handle transposition driving bolt (5-1) is converted into the long-distance linear reciprocating motion of the driven rack (5-5) by the displacement extension transmission device, and then converted into the clockwise rotation motion of the crank (5-8) by the driving device that turns straight into rotation, which is used to control the intermittent counterclockwise rotation of the door handle transposition shaft (2).

2. The disinfection device of door handle being rotational and transpositional according to claim 1, wherein the door handles (1) are evenly distributed along the door handle transposition shaft (2), the inner end of which is fixed with a shaft sleeve by a short shaft, coaxially connected to the door handle transposition shaft (2) by the shaft sleeve, nested in the arc groove of the door handle transposition shaft (2) by the short shaft, and can rotate around the axis of the door handle transposition shaft (2) along the arc groove.

3. The disinfection device of door handle being rotational and transpositional according to claim 1, wherein the unlocking device (4) only do linear reciprocating motion, and is used for controlling the opening and closing of the door; the unlocking device (4) comprises a switch bolt (4-1), a connecting rod of bolt (4-2) and a spring (4-3); the switch bolt (4-1) is fixedly connected with one end of the connecting rod of bolt (4-2), and the spring (4-3) is sleeved on one end of the connecting rod of bolt (4-2) that is closed to the switch bolt (4-1), and is used for controlling the reset of the switch bolt (4-1); the other end of the connecting rod of bolt (4-2) is provided with a stopper, and the dial (3-1) pushes the stopper when rotating, thus driving the unlocking device (4) to move.

4. The disinfection device of door handle being rotational and transpositional according to claim 1, wherein the disinfection method of the disinfection device (6) is heating disinfection, ultraviolet disinfection or disinfectant disinfection.

5. The disinfection device of door handle being rotational and transpositional according to claim 4, wherein when heating disinfection is adopted, a temperature controller and a time relay are provided in the disinfection device (6), the heating temperature is controlled by the temperature controller, and the heating time is controlled by the time relay, the back end of the disinfection device (6) is provided with the disinfection post-treatment device (7), and the disinfection post-treatment device (7) is a cooling fan;

when ultraviolet disinfection is adopted, a ultraviolet lamp and a time relay are provided in the disinfection device (6), the ultraviolet irradiation time is controlled by the time relay, and the disinfection post-treatment device (7) is not needed;

when disinfectant disinfection is adopted, a disinfectant storage tank, a spray device and an inductive switch are provided in the disinfection device (6), the spray of disinfectant is controlled by the inductive switch, the back end of the disinfection device (6) is provided with the disinfection post-treatment device (7), and the disinfection post-treatment device (7) is a fan for drying.

* * * * *